United States Patent [19]

Widner et al.

[11] Patent Number: 4,598,597
[45] Date of Patent: Jul. 8, 1986

[54] HAZARDOUS MATERIAL SAMPLING DEVICE

[75] Inventors: Rayburn K. Widner; John M. Tate, both of Arab, Ala.

[73] Assignee: The United States of America as represented by the Secretary of the Army, Washington, D.C.

[21] Appl. No.: 707,972

[22] Filed: Mar. 4, 1985

[51] Int. Cl.⁴ .............................................. G01N 1/04
[52] U.S. Cl. .................................... 73/864.41; 83/919
[58] Field of Search ............ 73/864.41, 863.01, 864.42, 73/864.43, 864.44, 864.45; 83/919

[56] References Cited

U.S. PATENT DOCUMENTS 4,304,139 12/1981 Johnson ...................... 73/864.41 X
4,383,394 5/1983 Qurnell et al. .................... 83/919 X
4,483,205 11/1984 Bellaiche et al. ............. 73/864.41 X

FOREIGN PATENT DOCUMENTS 931901 7/1963 United Kingdom .................. 83/919

Primary Examiner—Stewart J. Levy
Assistant Examiner—Tom Noland
Attorney, Agent, or Firm—Anthony T. Lane; Robert P. Gibson; Harold W. Hilton

[57] ABSTRACT

A remotely controlled apparatus for extracting samples of solid hazardous material from such items as solid propellant rocket motors. The device is pneumatically operated from a high pressure gas supply and includes a cutter assembly which extracts the sample. The cutter assembly is movable to different positions for successive sampling operations.

8 Claims, 7 Drawing Figures

HAZARDOUS MATERIAL SAMPLING DEVICE

DEDICATORY CLAUSE

The invention described herein may be manufactured, used, and licensed by or for the Government for governmental purposes without the payment to us of any royalties thereon.

BACKGROUND OF THE INVENTION

After missiles have been in the field or in storage for long periods of time, it may be necessary to extract samples of the solid propellant to determine the physical and chemical properties thereof. However, such extraction procedures can be extremely hazardous if done by a person in close proximity of the rocket motor.

It is, therefore, an object of the present invention to provide apparatus which is remotely controlled for extraction of samples of hazardous materials.

It is a further object of the present invention to provide such apparatus for removing samples of solid propellant from the motor of a rocket propelled missile.

SUMMARY OF THE INVENTION

A remotely controlled apparatus for extracting samples of hazardous materials from an object. The apparatus is a pneumatically operated device including an arm which is extendable from a pneumatic cylinder. A cutter is mounted on the distal end of the arm to cut samples of the hazardous material. The cylinder is mounted on a rotable support for rotation of the device to obtain a plurality of samples and control means is provided to extend and extract and rotate the cutter.

DESCRIPTION OF THE PREFERRED EMBODIMENT

Figure 1:
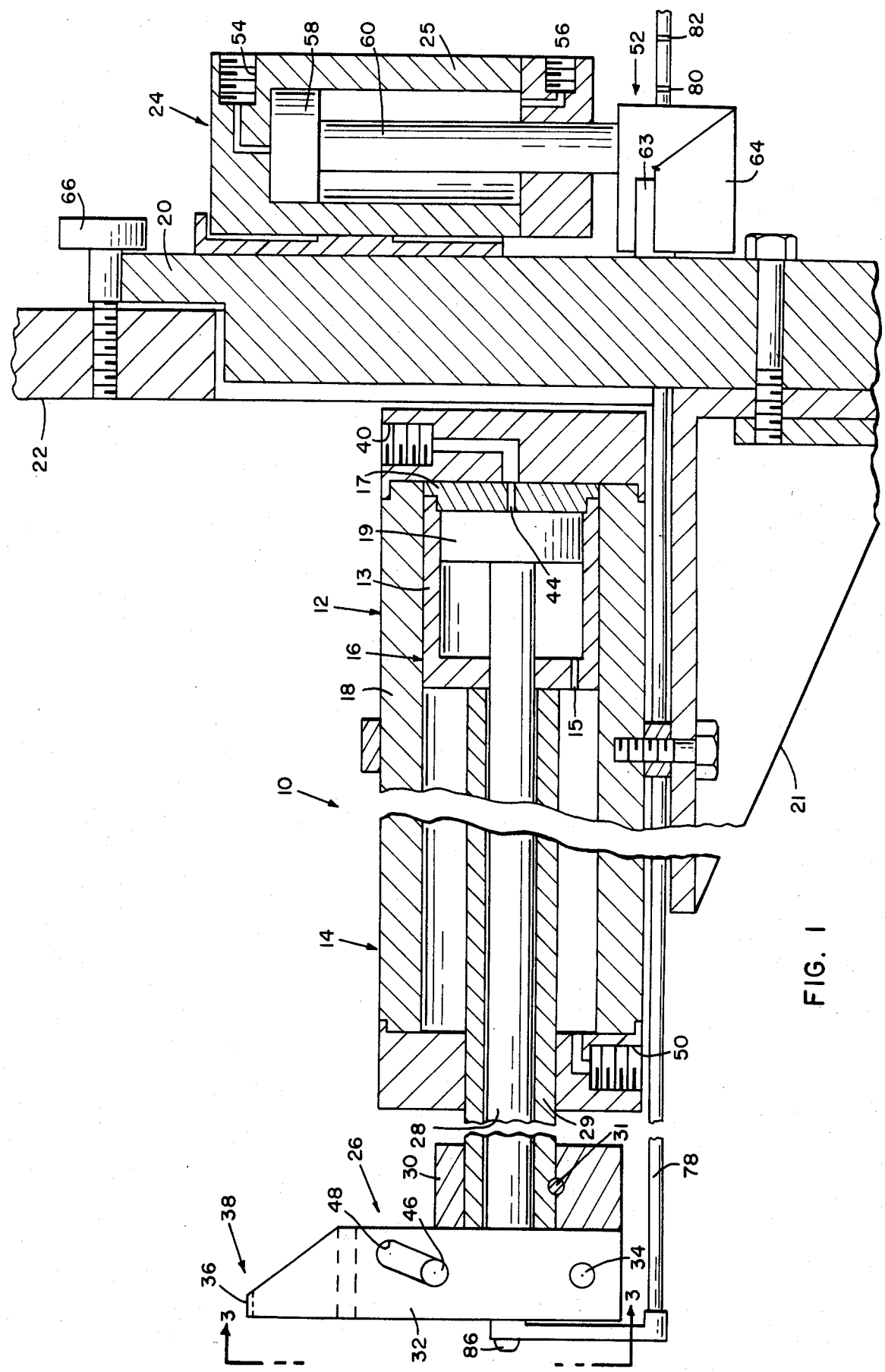
FIG. 1 is an elevational sectional view of the pneumatic cylinder and ratchet assembly of the present invention. The figure illustrates the cutter in the non-extended position prior to the sampling process.

As seen in FIG. 1, a pneumatic cylinder assembly 10 includes an aft section 12 and a forward section 14. A piston 16 is carried in the body 18 of the cylinder assembly and a second smaller piston 19 is carried in piston 16. Piston 16 includes a body portion 13 having an opening 15 therein and an aft member 17 secured to body portion 13. Cylinder assembly 10 is secured to a bracket 21 which is secured to a rotatable plate 20 which is mounted for rotation in a base plate 22. A positioning cylinder assembly 24 is secured to base plate 22 and is provided for rotation of mounting plate 20, as described hereinbelow, for a plurality of cutting operations.

A cutter assembly 26 is secured to a hollow shaft 29 which is secured to piston 16. A second shaft 28 is secured to piston 19 and extends through piston 16. The cutter assembly 26 includes a cutter mounting block 30 secured to the distal end of shaft 29 by a tapered pin 31. A cutter 32 is pivotably mounted on block 30 by a pin 34. Cutter 32 includes a blade member 36 at the upper end 38 thereof.

Figure 2:
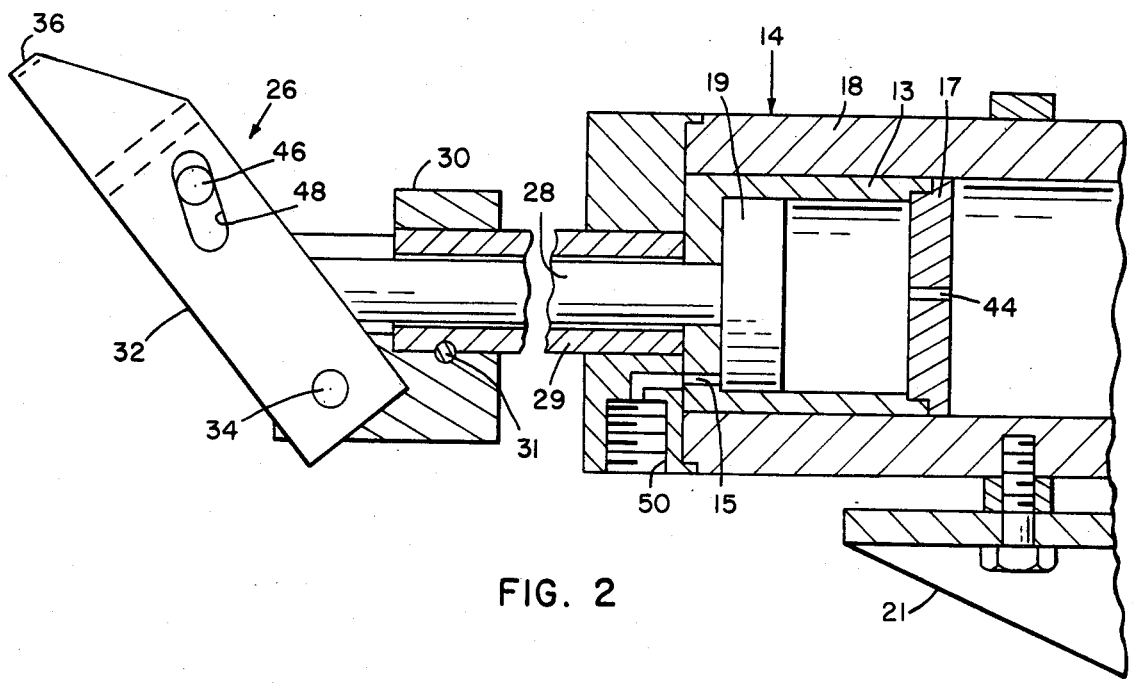
FIG. 2 is a partial elevational view of the pneumatic cylinder of FIG. 1 with the cutter in the extended position for the cutting process.

In a cutting operation a high presssure gas is directed through inlet 40 of cylinder body 18 for displacement of pistons 16 and 19 and shafts 28 and 29 to move the cutter assembly 26 into the cavity of the solid propellant rocket motor (not shown). After piston 16 has reached the end of its stroke, gas continues to flow through an inlet 44 in piston 16 to move the smaller piston 19 forward to the position shown in FIG. 2. This pivots the cutter 32 around pin 34 to move the blade 36 through the solid propellant. A yoke like support member 43 (FIG. 3) is secured to the distal end of shaft 28 and includes a pair of pins 46 which supports the cutter 32 thereon. The pins 46 extend through a pair of grooves 48 on opposite sides of the cutter 32.

To retract the cutter, gas is directed through inlet 50 in the forward section 14 of cylinder 18 to the backside of piston 16 to move the position back to its retracted position shown in FIG. 1. When piston 16 reaches this position, gas is continued to be directed through openings 15 of piston 16 to the backside of piston 19 to move piston 19 to its retracted position shown in FIG. 1.

Figure 4:
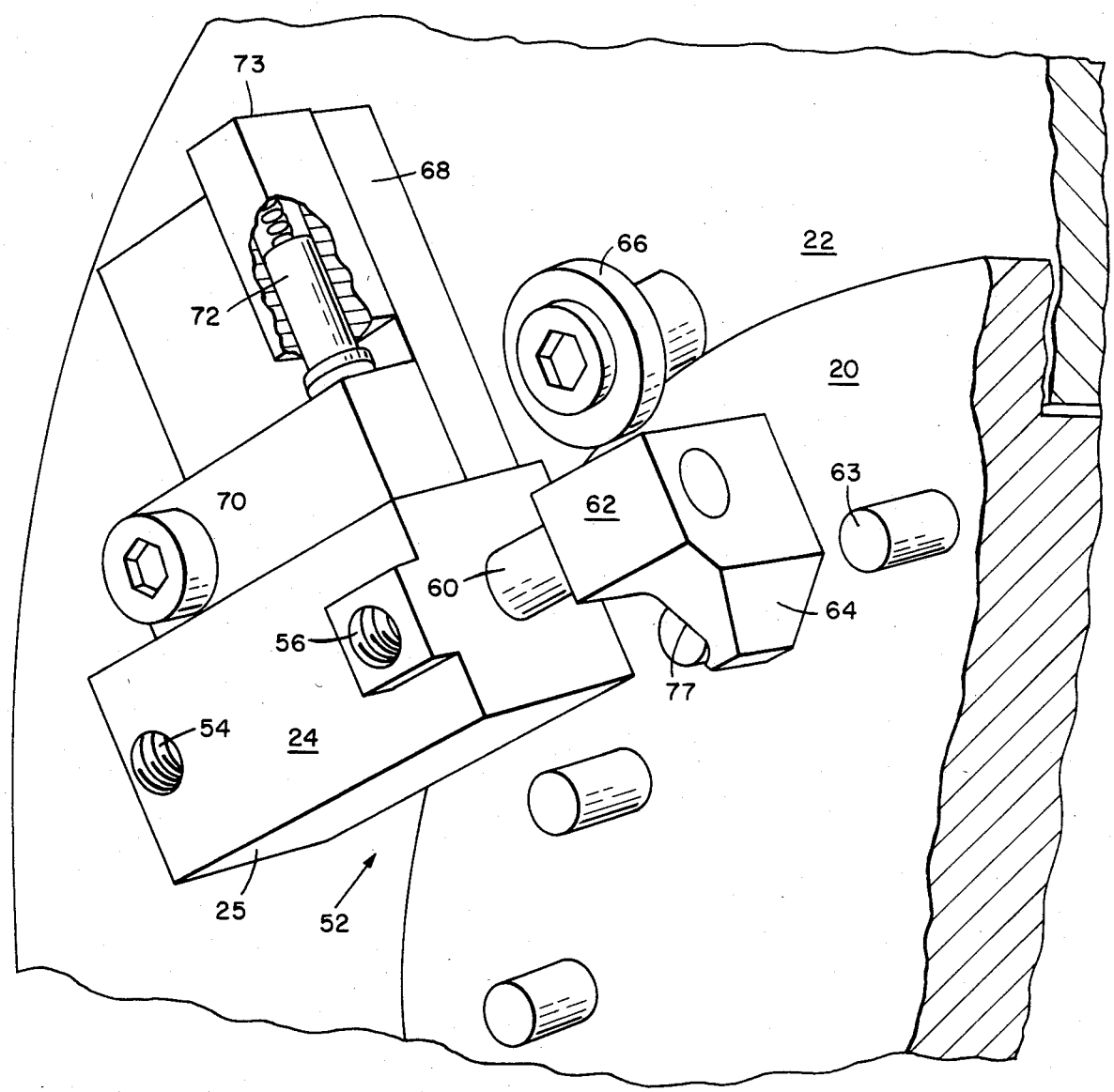
FIG. 4 is a partial pictorial view of the ratchet assembly for rotating the assembly for successive cutting operations.

After the cutter has been retracted and if it is desired to obtain additional samples of propellant, positioning cylinder assembly 24 is activated for operation of a ratchet assembly 52 mounted on the backside of base plate 22 for rotation of mounting plate 20 in base plate 22 to reposition the cutting assembly. (FIGS. 1 and 4).

The mechanism for rotating cylinder 18 includes positioning assembly cylinder 24 and ratchet assembly 52. Assembly 24 includes a cylinder housing 25 having inlet and outlet ports 54 and 56, respectively, at opposite ends thereof. A piston 58 is carried in cylinder housing 25 and a rod 60 is secured to piston 58 and extends out of cylinder housing 25. A ratchet pawl 62 is secured to the distal end of rod 60 and includes an angled surface 64 thereon. A plurality of ratchet positioning pins 63 are secured around carrier plate 20 for engagement by ratchet pawl 62 in a manner described hereinbelow. Carrier plate 20 is attached to base plate 22 by a plurality (typically six) of equally spaced support and centering assemblies 66 which are attached to base plate 22 and rotatably support the carrier plate 20 on the base plate.

The positioning cylinder assembly 24 is secured to a ratchet mount 68 by a pivot bolt 70. Ratchet mount 68 is rigidly secured to base plate 22.

To rotate carrier plate 20 for successive cutting operations, gas pressure is directed into inlet 54 of cylinder 25 housing to move piston 58 and extend rod 60 out of cylinder housing 25. This movement forces angled surface 64 of ratchet pawl 62 into contact with one of the ratchet pins 63 which pivots positioning cylinder assembly 24 about pivot bolt 70 so that the pawl 62 clears pin 63. A spring loaded plunger 72 is carried in a housing 73 which is secured to rachet mount 68. The plunger biases cylinder housing 25 so that one of the pins 63 is nestled in a curved portion 77 of ratchet pawl 62 for gripped engagement thereby. Gas pressure is then directed through inlet 56 to move piston 58 back to its original position. This movement retracts rod 60 into cylinder 25 and since pawl 62 is secured to rod 60 the pawl displaces pin 63 for rotation of carrier plate 20 to place cutter 26 for position for another cutting operation.

Figure 6:
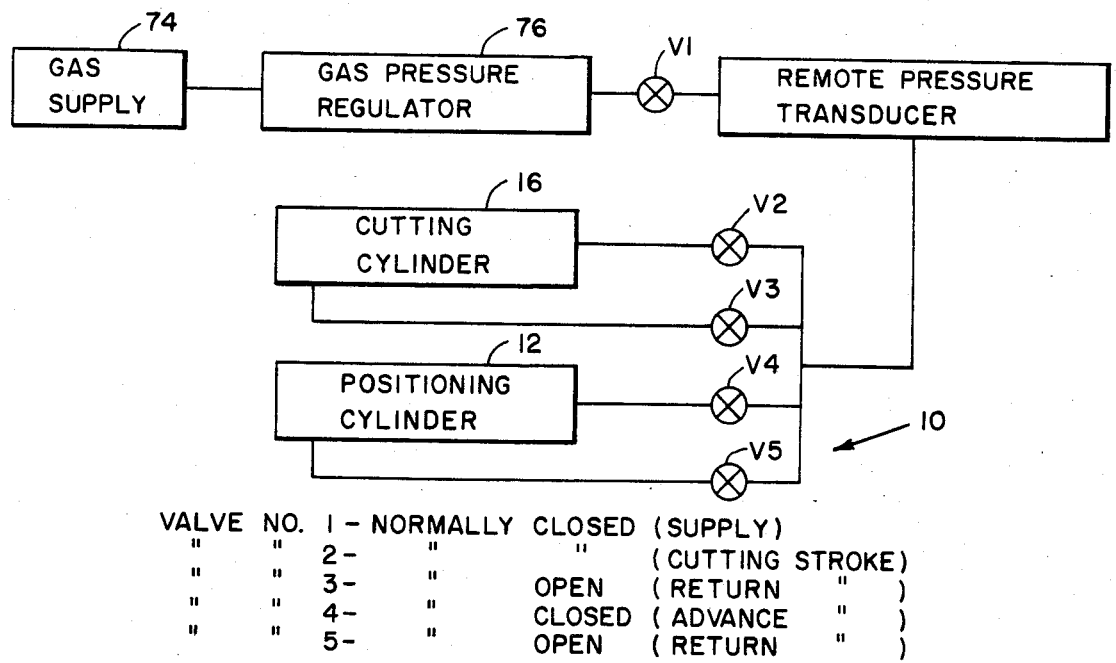
FIG. 6 is a block diagram of the control mechanism for operating the sampling device from a remote control station.
Figure 7:
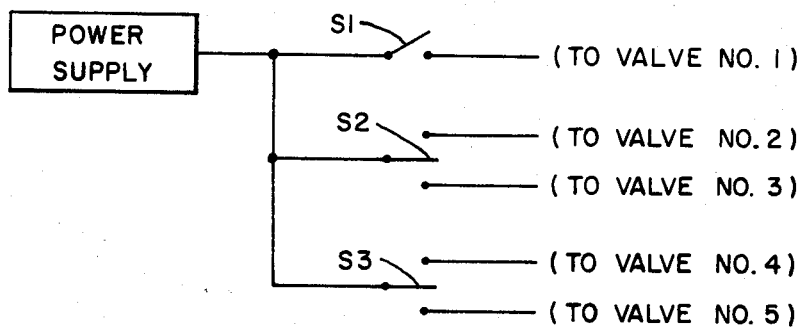
FIG. 7 is a schematic diagram of the electrical control system for remotely operating the apparatus of the present invention.

FIGS. 6 and 7 illustrate the remote operation procedures for the sampling device. The device is pneumatically operated from a high pressure gas supply 74. The gas is regulated by a regulator 76 to produce the desired force for extracting the sample. After the sample cutter is positioned it can be moved to additional positions remotely. This is accomplished by the positioning cylinder 12.

The sequence of operation is described in conjunction with FIGS. 6 and 7 as follows:
1. Turn on gas supply 74.
2. Set gas reglator 76 to desired pressure.
3. Close switch (S1), this opens the gas supply to the cylinders.
4. Move switch (S2) to cut position this opens valve V2.
5. After the cutter has made a cutting operation, move switch (S2) to retract position this returns the pistons to the retract position.
6. If additional cuts are needed place switch (S3) to the rotate positon this opens valve 4 to supply gas to positioning cylinder to move the piston 58 to extended position for engagement of the pawl with a pin on the rotatable plate.
7. Move switch (S3) to the retract position this retracts piston 58 and the pawl which displaces the pin.

Figure 3:
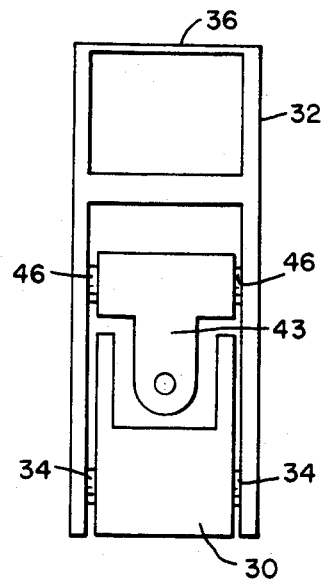
FIG. 3 is an elevational view taken along line 3—3 of FIG. 1.
Figure 5:
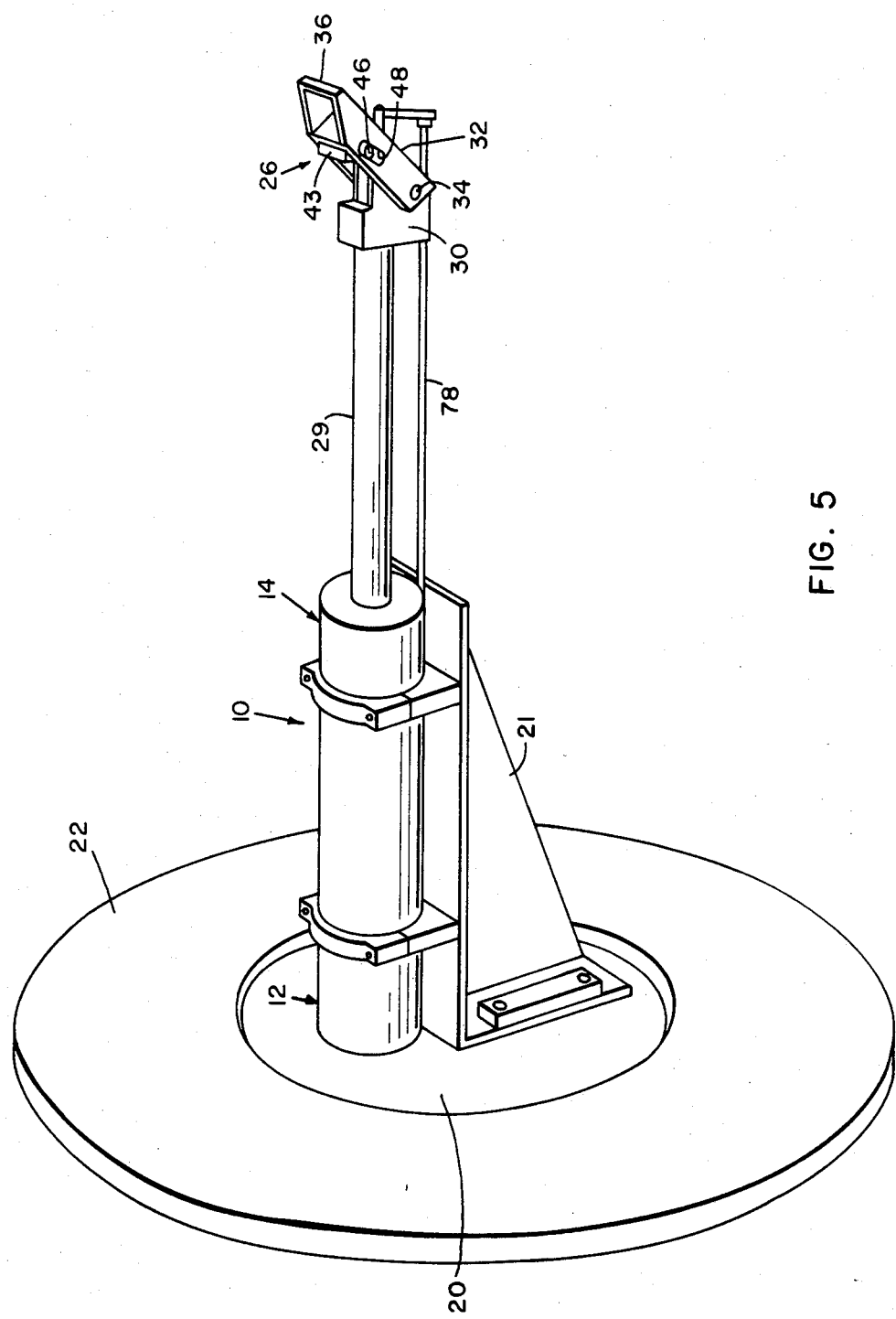
FIG. 5 is a pictorial view of the assembly illustrating the cutter in the extended position.

As seen in FIGS. 1 and 5, a locator rod 78 is attached to the cutter and extends through base plate 22. The rod is marked at two places 80 and 82 to indicate the position of the cutter, (i.e., prior to or after the cutter has cut a sample). A television camera is located near the apparatus to indicate the position of the locator rod and, therefore, the position of the cutter on a television receiver in the remote control room. Locator rod 78 is secured to the yoke support member 43 by a screw 86 which also secures the yoke support member 43 to the distal end of the inner piston rod 28. FIG. 3 illustrates the yoke support member 43 mounted in cutter 32 with the locator rod 78 removed for clarity. Also for the sake of clarity the locator rod has not been illustrated in FIG. 2.

Once the samples are cut they may be allowed to fall into a container (not shown) and retrieved after the cutting operations.

We claim:

1. Apparatus for extracting samples of hazardous materials from an object comprising:
   a. a source of gas pressure;
   b. a first cylinder having a pair of pistons therein; the first of said pair of pistons being hollow and having a first hollow shaft extending therefrom, the second of said pair of pistons being concentrically mounted in said first piston and having a second shaft thereon, said second shaft extending through said first hollow shaft;
   c. a cutter block assembly secured to the distal end of said first shaft,
   d. a cutter assembly pivotably mounted on said cutter block assembly for cutting said hazardous material responsive to movement of said pistons to an extended position from said cylinder,
   e. control means for directing said source of gas to said pistons for movement thereof to the extended position.

2. Apparatus as in claim 1 wherein said first piston includes a body portion having an aft plate member secured thereto, said body portion and said aft plate member each provided with an opening therethrough, whereby responsive to the first piston being placed in the extended position, said gas is directed through the opening in said aft plate member for further movement of said second piston for rotation of said cutter assembly for cutting through said hazardous material.

3. Apparatus as in claim 2 wherein said cutter assembly includes a yoke member secured to the distal end of said first shaft, said yoke member having a pair of pins extending from opposite sides thereof, said cutter assembly including a cutter member having grooves therein to receive said pins of said yoke member.

4. Apparatus as in claim 3 wherein said first cylinder is mounted on a rotatable plate, said rotatable plate being mounted on a stationary base plate.

5. Apparatus as in claim 4 including means for rotating said rotatable plate.

6. Apparatus as in claim 5 wherein said means for rotating said rotatable plate includes a second cylinder mounted on said base plate, a third piston carried in said second cylinder, a piston rod secured to said third piston and extending out of said second cylinder, a pawl secured to the distal end of said piston rod, a plurality of pins secured on said rotatable plate for gripped engagement by said pawl in response to said piston rod being moved to an extended position, said piston rod disposed for displacing said plurality of pins in response to said third piston being moved to a retracted position.

7. Apparatus as in claim 6 including biasing means for biasing said second cylinder for the gripped engagement by said pawl of one of said plurality of pins.

8. Apparatus as in claim 7 including locator means for indicating the position of said cutter responsive to displacement of said first and second pistons.

* * * * *